Figure 1:
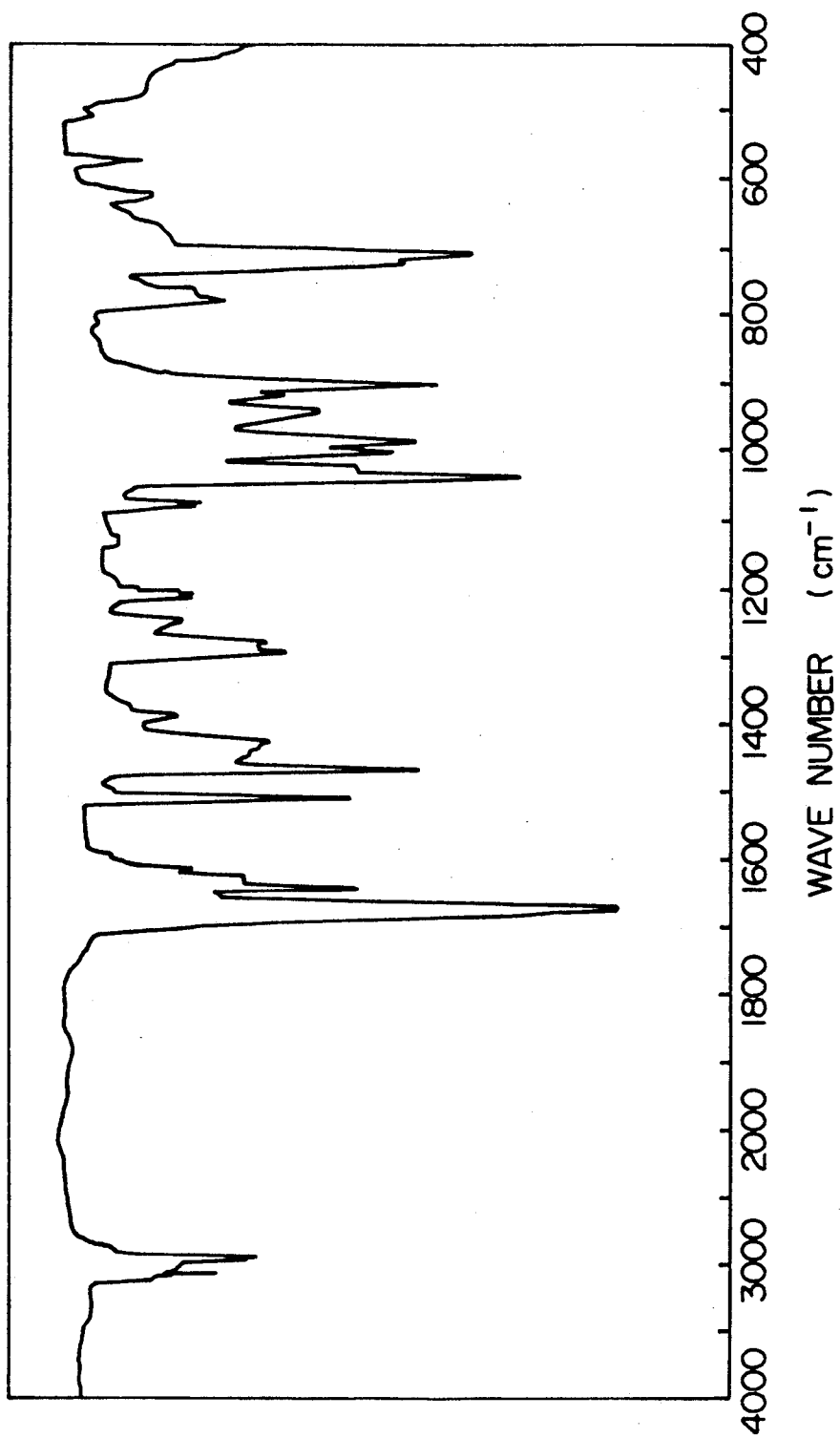

United States Patent [19]

Matsuoka et al.

[11] Patent Number: 5,214,116
[45] Date of Patent: May 25, 1993

[54] RESIN DERIVED FROM SULFUR-CONTAINING UNSATURATED COMPOUND AND HAVING A HIGH REFRACTIVE INDEX

[75] Inventors: Singo Matsuoka; Masahiro Amano, both of Shinnanyo; Yasuji Kida, Kudamatsu, all of

[73] Assignee: Tokuyama Soda Kabushiki Kaisha, Yamaguchi, Japan

[21] Appl. No.: 804,546

[22] Filed: Dec. 11, 1991

Related U.S. Application Data

[63] Continuation of Ser. No. 476,346, Feb. 7, 1990, abandoned.

[30] Foreign Application Priority Data

Feb. 7, 1989 [JP] Japan ................................. 1-26700

[51] Int. Cl.$^5$ ............................................. C08F 28/02
[52] U.S. Cl. .................................. 526/286; 351/159; 526/289
[58] Field of Search ............................. 526/286, 289

[56] References Cited

U.S. PATENT DOCUMENTS 4,931,521 6/1990 Matsuda ......................... 526/286

FOREIGN PATENT DOCUMENTS 273710 7/1988 European Pat. Off. .
246511 8/1974 U.S.S.R. .

OTHER PUBLICATIONS

Chemical Abstracts, vol. 112, 19th Mar. 1990, p. 14, Abstract No. 99463u.

Primary Examiner—Christopher Henderson
Attorney, Agent, or Firm—Sherman and Shalloway

[57] ABSTRACT

There is provided a resin having a high refractive index. The resin is a polymer comprising units derived from a sulfur-containing unsaturated compound. The present invention also provides novel sulfur-containing unsaturated compounds which in useful in the production of the resin. Examples of these compounds include

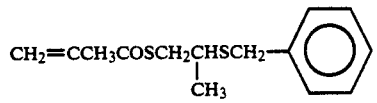

and $CH_2=CCH_3COSCH_2CH_2SC_3H_6SCH_3$.

3 Claims, 2 Drawing Sheets

RESIN DERIVED FROM SULFUR-CONTAINING UNSATURATED COMPOUND AND HAVING A HIGH REFRACTIVE INDEX

This application is a continuation of application Ser. No. 07/476,346, filed Feb. 7, 1990, now abandoned.

This invention relates to a resin having a high refractive index More specifically, it relates to a resin having a high refractive index which is derived from a sulfur-containing unsaturated compound and is suitable as an optical material such as an eyeglass lens, a prism or an optical disc.

Synthetic resins which may supersede inorganic glass have been variously studied in the past. But because of their many defects, such synthetic resins having fully satisfactory properties have not been obtained. Polymers obtained by polymerizing monomers containing methyl methacrylate or ethylene glycol bis-(allyl carbonate) as a main component are used as optical resins or lenses, but their refractive indices are as low as about 1.50.

Various resins having higher refractive indices have been proposed. For example, polycarbonate or polysulfone type resins having high refractive indices have been proposed. These resins have a refractive index of as high as about 1.60, but still have various problems to be solved. For example, they have a low light transmittance, lack optical uniformity, or may be colored.

Various crosslinkable monomers have been proposed for production of resins having a high refractive index. For example, EP 273710 A2 proposes polyfunctional thiomethacrylates typified by

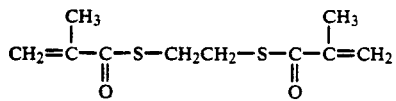

as a starting monomer for resins having a high refractive index.

The polyfunctional thiomethacrylates excel as monomers known heretofore in that they give transparent resins having a refractive index close to 1.6. The refractive index of 1.6, however, is not on a fully satisfactory level. In addition, the polyfunctional thiomethacrylates are technically difficult to produce, and the speed of polymerization is also difficult to control. Hence, they do not prove to be industrially fully satisfactory as starting monomers for obtaining resins having high refractive resins.

USSR Patent No. 246511 proposes monomers of the following formulae $$CH_2=CHCOSCH_2CH_2SC_4H_9$$

as materials for the production of rubbers for special uses. The Russian Patent, however, describes nothing specifically on the polymerization of the above monomers and the rubbers for special uses.

Japanese Laid-Open Patent Publication No. 1626711988 discloses that thiolcarboxylic acid esters represented by the following formula

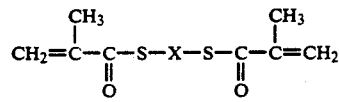

wherein X is $-CH_2CH_2SCH_2CH_2-$, $-CH_2CH_2OCH_2CH_2-$ or $-CH_2CH_2-$, are useful as monomers which give transparent resins having a high refractive index, useful as an optical plastic material.

The present inventors have long been engaged in the production and research work on transparent resins having high refractive indices, and have aimed at developing transparent resins having a refractive index of at least 1.62 and an Abbe number of at least 30 which are the ultimate needs in the use of the resins as optical materials. As a result, the inventors discovered highly refractive index resins which fully meet these needs. On further investigations, the inventors have succeeded in perfecting resins having a high refractive index which are industrially easy to handle and produce.

It is an object of this invention to provide a transparent resin having a high refractive index.

Another object of this invention is to provide a resin having a refractive index of at least 1.62, preferably at least 1.63, and an Abbe number of at least 30, preferably at least 32.

Still another object of this invention is to provide a novel monomer which gives a resin having an high refractive index with an easy control of the rate of polymerization.

Other objects and advantages will become apparent from the following description.

According to the invention, the above objects and advantages of the invention are firstly achieved by a resin having a high refractive index, said resin being a polymer comprising units derived from a sulfur-containing unsaturated compound represented by the following formula (I)

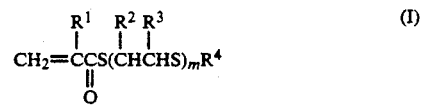

wherein $R^1$ represents a hydrogen atom or a methyl group; $R^2$ and $R^3$ are identical or different, and each represents a hydrogen atom or an alkyl group having 1 to 5 carbon atoms; $R^4$ represents a substituted or unsubstituted alkyl group having 1 to 5 carbon atoms, a substituted or unsubstituted aralkyl group having 7 to 10 carbon atoms or a substitutted or unsubstituted aryl group having 6 to 10 carbon atoms, the substituent of each of the substituted groups being selected from the class consisting of halogen atoms excluding a fluorine atom, alkyl groups having 1 to 5 carbon atoms, alkoxy groups having 1 to 5 carbon atoms, alkylthio groups having 1 to 5 carbon atoms, a phenyl group and a phenylthio group; and m is an integer of at least 1.

Figure 2:
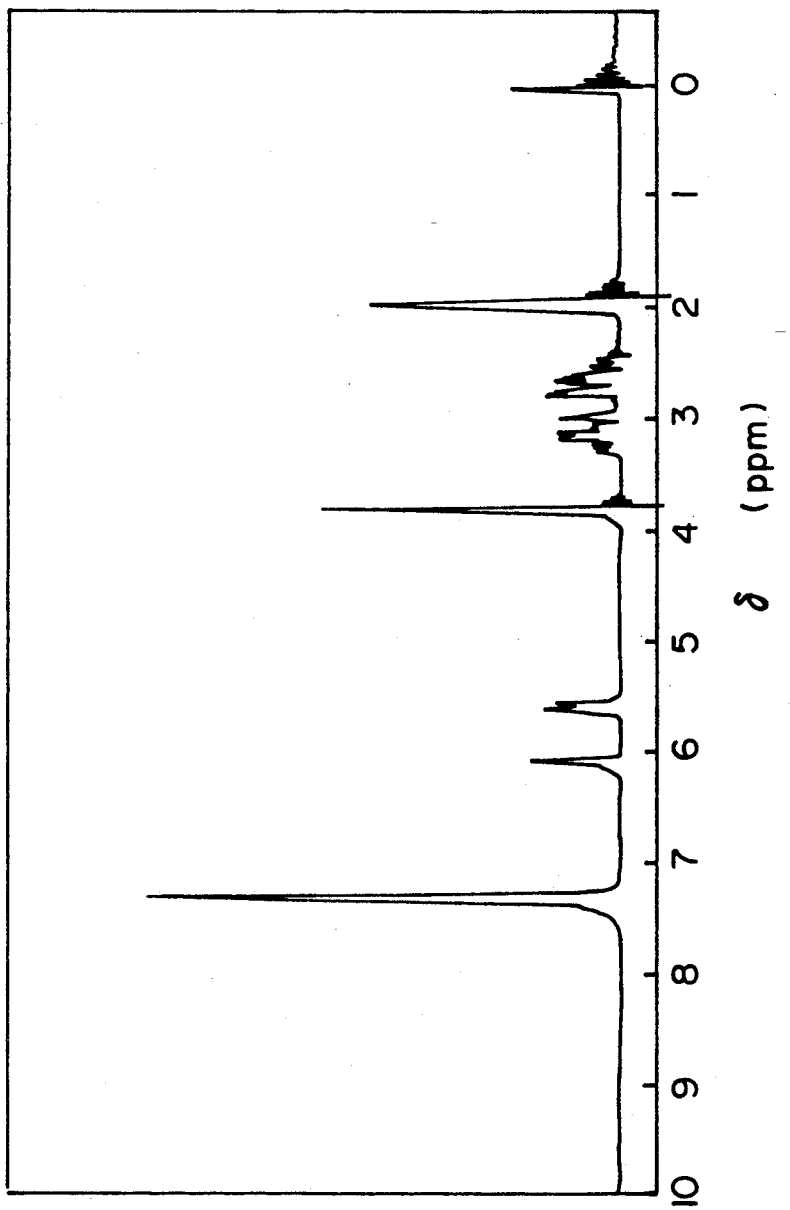

FIGS. 1 and 2 accompanying this application are an infrared absorption spectrum chart and a $^1$H-NMR spectrum chart respectively of the thiocarboxylic acid ester obtained in Example 1.

The sulfur-containing unsaturated copolymer constituting the polymer units is represented by formula (I).

In formula (I), $R^1$ represents a hydrogen atom or a methyl group, preferably the methyl group.

$R^2$ and $R^3$ are identical or different and each represents a hydrogen atom or an alkyl group having 1 to 5 carbon atoms, preferably the hydrogen atom. The alkyl group may be linear or branched, and examples include methyl, ethyl, propyl, butyl and pentyl groups. Methyl and ethyl groups are preferred as the alkyl group, and the methyl group is especially preferred.

$R^4$ represents a substituted or unsubstituted alkyl group having 1 to 5 carbon atoms, a substituted or unsubstituted aralkyl group having 7 to 10 carbon atoms, or a substituted or unsubstituted aryl group having 6 to 10 carbon atoms. The unsubstituted alkyl group for $R^4$ may be linear or branched, and its examples may be the same as those cited for $R^2$.

The unsubstituted aralkyl groups having 7 to 10 carbon atoms are preferably those represented by the following formula

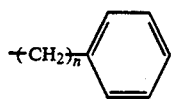

wherein n is an integer of 1 to 4, are preferred. Examples are benzyl, phenylethyl, phenylpropyl and phenylbutyl groups.

Phenyl and naphthyl groups may be cited as the unsubstituted aryl group having 6 to 10 carbon atoms.

The alkyl, aralkyl and aryl groups for $R^4$ may be substituted by a halogen atom excluding a fluorine atom, an alkyl group having 1 to 5 carbon atoms, an alkoxy group having 1 to 5 carbon atoms, an alkylthio groups having 1 to 5 carbon atoms, a phenyl group or a phenylthio groups. The halogen atom may include chlorine, bromine and iodine atoms. The fluorine atom cannot be used because it cannot increase the refractive index of the polymer. The alkyl group having 1 to 5 carbon atoms may be linear or branched, and examples include methyl, ethyl, propyl and pentyl groups. The alkoxy group having 1 to 5 carbon atoms may be linear or branched, and its examples include methoxy, ethoxy, propoxy, butoxy and pentoxy groups. The alkylthio group having 1 to 5 carbon atoms may be linear or branched, and includes, for example, methylthio, ethylthio, propylthio, butylthio and pentylthio groups.

Typical and preferred examples of alkyl, aralkyl and aryl groups substituted by these substituents include haloaralkyl groups such as chlorophenylmethyl, dibromophenylmethyl and tribromophenylmethyl groups; haloalkyl groups such as chloromethyl, bromomethyl and trichloromethyl groups; haloaryl groups such as chlorophenyl, bromophenyl, dichlorophenyl, dibromophenyl and tribromophenyl groups; and methylthiophenyl, di(methylthio)phenyl, phenylthiophenyl, biphenyl, methylthiophenylmethyl, di(methylthio)phenylmethyl, tolyl, xylyl, and methylphenylmethyl groups.

In formula (I), m is an integer of at least 1. Generally, as the m becomes larger, the content of sulfur per molecule becomes higher, and the polymer resulting from polymerization has a higher refractive index, and higher impact strength. If, however, it becomes too large, the viscosity of the compound of formula (I) increases abruptly and is difficult to handle. The polymer obtained from it tends to have reduced thermal resistance. When the refractrive index, impact strength and thermal resistance of the resulting polymer are considered, it is advantageous to select m within the range of 1 to 5, especially 1 to 3.

Among the compounds of formula (I), those of the following formulae (II) and (III) are novel compounds and are preferred because they have a high refractive index, a large Abbe number give polymers having excellent thermal resistance.

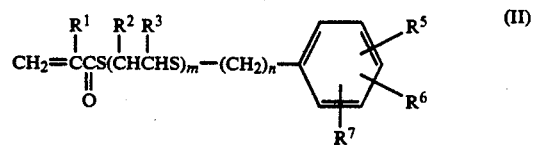

wherein $R^1$, $R^2$, $R^3$ and m are as defined above; n is 1 to 4; and $R^5$, $R^6$ and $R^7$ are identical or different and each represents a hydrogen atom, a halogen atom excluding a fluorine atom, an alkyl group having 1 to 5 carbon atoms, an alkylthio group having 1 to 3 carbon atoms, a phenyl group, a phenylthio group or an alkoxy group having 1 to 5 carbon atoms.

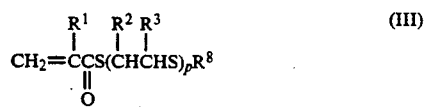

wherein $R^1$, $R^2$, and $R^3$ are as defined above, p is 2 to 6; and $R^8$ represents an alkyl group having 1 to 5 carbon atoms.

The sulfur-containing compound represented by formulae (II) and (III) are novel compounds and constitute part of the invention.

The sulfur-containing unsaturated compounds represented by formula (II) particularly can give polymers having a high refractive index, a large Abbe number, good impact strength and excellent hardness. For example by using the sulfur-containing unsaturated compounds of formula (II), polymers having a refractive index of at least 1.62, especially at least 1.63 and an Abbe number of at least 32, and especially at least 33 can be obtained.

The sulfur-containing unsaturated compounds of formula (III) are especially characteristic in that they give polymers having a large Abbe number of, for example, at least 33. However, as compared with the compounds of formula (II), the compounds of formula (III) generally tend to give polymers having a lower refractive index. Of the compounds of formula (III), those of formula (III) in which p is 1, but the resulting polymers having a higher refractive index than compounds of formula (III) in which p is 1, but the resulting polymers tend to have a smaller Abbe number and lower hardness. Thus, the compounds of formula (III) have the advantage that the refractive index, Abbe number and hardness of the resulting polymers can be adjusted to the desired values. The properties of the polymers obtained are not controlled only by the value of p in formula (III). They can also be controlled by the type of $R^8$.

The following examples may be given as the sulfur-containing unsaturated compounds of formula (I) including formulae (II) and (III).

| | |
|---|---|
| $CH_2=CHCOSC_2H_4SC_2H_5$, | (100) |
| $CH_2=CCH_3COS(C_2H_4S)_2CH_3$, | (102) |
| $CH_2=CCH_3COS(C_2H_4S)_3CH_3$, | (104) |

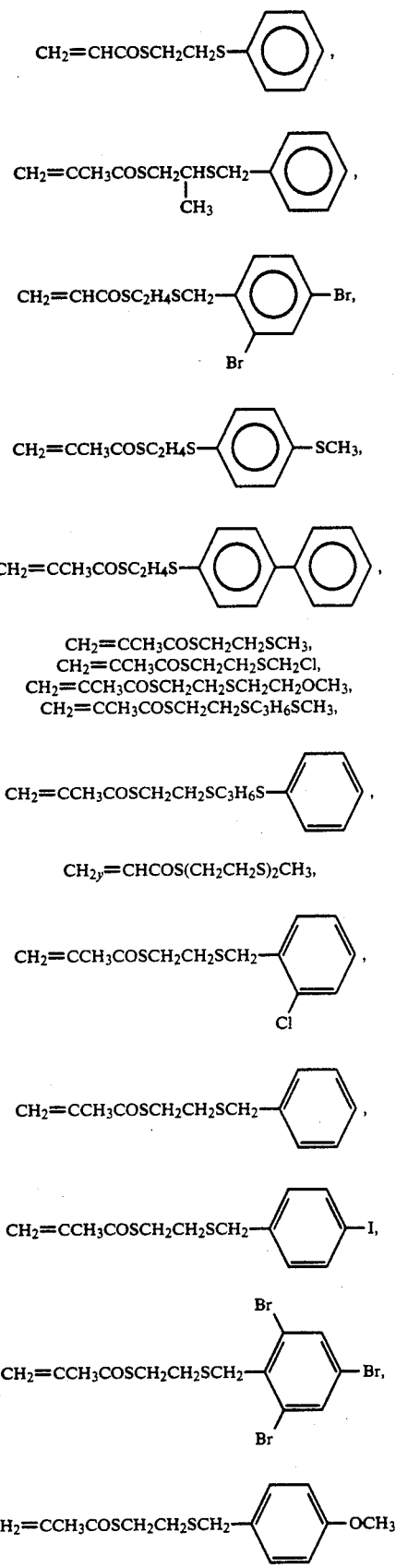
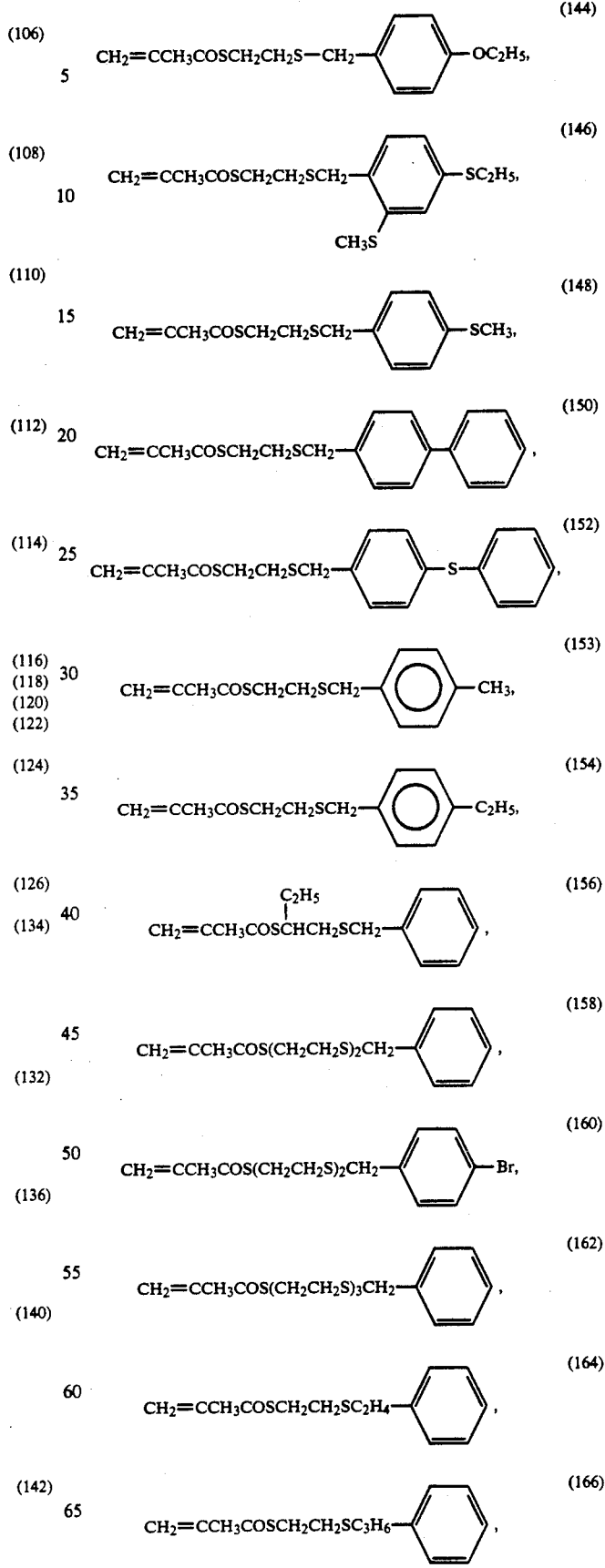

-continued

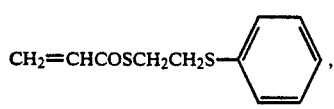 (168)

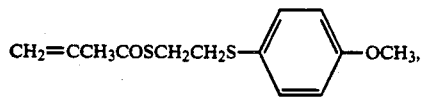 (170)

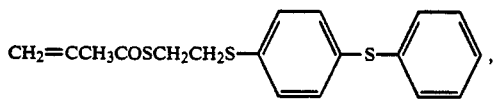 (172)

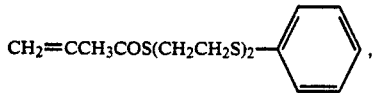 (174)

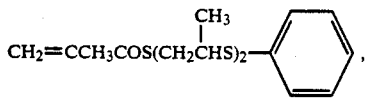 (176)

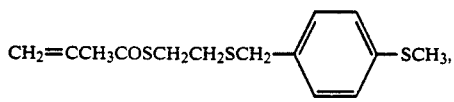 (182)

$CH_2=CHCOSC_2H_4SCH_3$ (184)
$CH_2=CCH_3COSC_2H_4SC_2H_5$ (186)
$CH_2=CHCOS(C_2H_4S)_3CH_3$ (188)
$CH_2=CHCOS(C_2H_4S)_4CH_3$ (190)
$CH_2=CHCOS(C_2H_4S)_5CH_3$ (192)

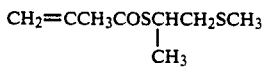 (194)

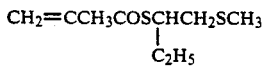 (196)

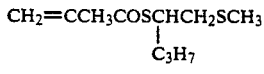 (198)

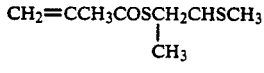 (200)

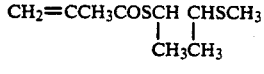 (202)

$CH_2=CCH_3COSC_2H_4SCH_2SCH_3$ (204)

(206)

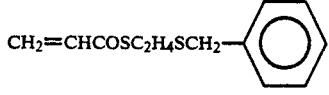

(208)

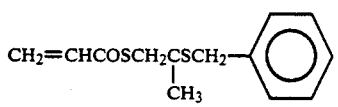

-continued

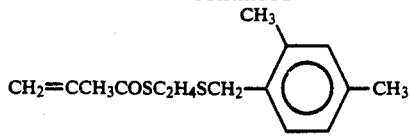 (210)

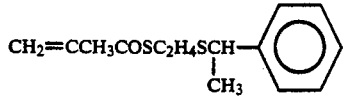 (212)

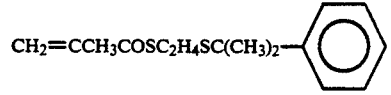 (214)

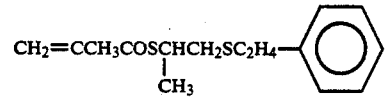 (216)

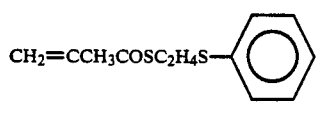 (218)

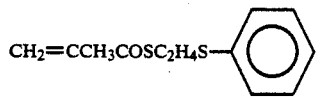 (220)

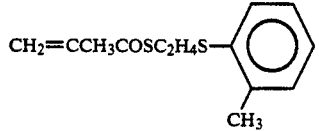 (222)

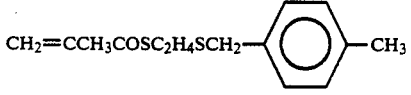 (224)

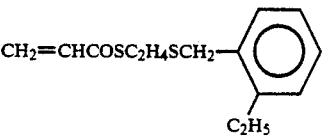 (226)

Many of the sulfur-containing unsaturated compounds of formula (I) are novel. The sulfur-containing unsaturated compounds of formula (I) can be identified and determined by the following methods (i) to (iii).

(i) By measuring their infrared spectra (IR), an absorption based on the CH bonding can be observed at 3150—2800 cm$^{-1}$, an absorption based on the terminal double bond can be observed at 1650 to 1620 cm$^{-1}$. Also a strong absorption of the carbonyl group based on the thioester bond can be observed at about 1660 to 1690 cm$^{-1}$.

(ii) The compounds can be easily identified by measuring $^1$H-NMR spectrum. In particular, when R$^1$ in formula (I) is a methyl group, a peak based on the methyl group, a peak based on the terminal vinylidene proton, and a peak based on the terminal vinyldene proton, can be observed in a ratio of 3:1:1 at about δ1.9 ppm, δ5.7 ppm and δ6.1 ppm as a pattern peculiar to a methacrylate. If $R^1$ is a hydrogen atom, three protons are observed at $\delta 5.6$ to 7 ppm as a pattern peculiar to an acrylate. Furthermore, in a thioetehr, hydrogen on a carbon atom bonded to a sulfur atom shows a peak of a pattern according to the state of bonding at near 2.9 ppm. Furthermore, if $R^2$, $R^3$ and $R^4$ each show a methyl group, a doublet is seen near at $\delta 1.1$ ppm. When an atomatic proton exists, a peak is seen at $\delta 7$ to 8.5 ppm. If an aliphatic hydrogen exists, a peak is observed at $\delta 1$ to 2 ppm. If other hydrogen atoms are present, a spectral pattern is shown according to the manner of bonding of these hydrogen. The compound can be easily identified from the above information.

(iii) The weights in % of carbon, hydrogen and sulfur are determined by elemental analysis. If the total sum of the weight percents of the elements recovnized is subtracted from 100, the weight percent of oxygen can be calculated. Thus, the composition formula of the compound can be determined.

The sulfur-containing unsaturated compounds of formula (I) can be advantageously produced, for example, by reacting a compound of formula (A)

  (A)

wherein $R^2$, $R^3$, $R^4$ and m are as defined, with a compound of formula (B)

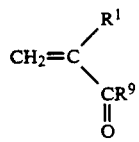  (B)

wherein $R^1$ represents a hydrogen atom or a methyl group and $R^9$ represents a hydroxyl group, a chlorine atom or an alkoxy group.

The method will be described with regard to the case where the compound of formula (B) is a carboxylic acid (when $R^9$ is a hydroxyl group), it is a carboxylic acid chloride (when $R^9$ is a chlorine arom) and it is a carboxylic acid ester (when $R^9$ is an alkoxy group).

(a) Method in which a carboxylic acid is used

The compound of formula (A) and a carboxylic acid of formula (B) in which $R^9$ is a hydroxyl group are dehydrocondensed in the presence of an acid catalyst to give a sulfur-containing unsaturated compound of formula (I). The mole ratio of the starting materials charged may be properly determined as required. It is recommended to use one of them usually in an excessive amount. Examples of the acid used as the catalyst in the reaction are mineral acids such as hydrochloric acid and sulfuric acid, aromatic sulfonic acids and Lewis acids such as boron trifluoride etherate.

In this reaction, water is formed as a byproduct. Since this reaction is an equilibrium reaction, it is generally preferable to remove water from the reaction system by using a Dean Stark water separator, by putting a dehydrating agent such as anhydrous sodium sulfate or molecular sieve in a Soxhlet extractor and refluxing a solvent, or by causing the copresence of a dehydrating agent such as N,N-dicyclohexylcarbodiimide in the reaction system. The solvent is preferably an aromatic hydrocarbon such as benzene or toluene, or a halogenated aliphatic hydrocarbon such as chloroform or dichloromethane.

The reaction temperature differs depending upon the type of the solvent, but generally, reaction temperatures of 0° to 120° C. are preferred. The reaction time cannot be generically determined. It is especially preferred from 30 minutes to 20 hours, especially from 1 to 6 hours. There is no particular limitation on the method of isolating the final product of formula (I) from the reaction mixture and purifying it, and any known methods can be used.

(b) Method in which a carboxylic acid chloride is used

The compound of formula (A) and a carboxylic acid chloride of formula (B) in which $R^9$ is a chlorine atom are subjected to dehydrochlorination in the presence of a base to give a sulfur-containing unsaturated compound of formula (I). Usually the mole ratio of the compound of formula (A) to the compound of formula (B) may be selected from the range of 0.8 to 1.5. It is especially preferred to use them in equimolar proportions.

In this reaction, hydrogen chloride is formed as a by-product. In order to remove hydrogen chloride from the reaction system, it is generally preferred to cause the presence of a base as a hydrogen chloride scavenger in the reaction system, or by passing an inert gas such as nitrogen through the reaction system.

Known bases may be used as the hydrogen chloride scavenger. Examples include trialkylamines such as trimethylamine, triethylamine, tripropylamine, pyridine, tetramethylurea, sodium hydroxide and sodium carbonate. The amount of the base may be at least 1 mole per mole of the carboxylic acid chloride.

It is generally preferable to use an organic solvent in the above reaction. Examples of suitable solvents include aliphatic or aromatic hydrocarbons and halogenated hydrocarbons such as benzene, toluene, xylene, hexane, heptane, petroleum ether, chloroform, methylene chloride and ethylene chloride; ethers such as diethyl ether, dioxane and tetrahydrofuran; N,N-dialkylamides such as N, N-dimethylformamide and N,N-diethylformamide; and dimethyl sulfoxide.

The temperature for the reaction may be selected from a broad range. It is generally $-20°$ to 100° C., preferably 0° to 50° C. The reaction time differs according to the types of the starting materials. Usually, it is 5 minutes to 24 hours, preferably 10 minutes to 4 hours. Preferably, the reaction is carried out with stirring.

There is no particular limitation on the method of isolating the desired compound of formula (1) from the reaction mixture and purifying it, and any known methods can be used for these purposes.

(c) Method in which a carboxylic acid ester is used

The compound of formula (A) and a carboxylic acid ester of formula (B) in which $R^9$ is an alkoxy group are subjected to ester-interchange to give a thiocarboxylic acid ester of formula (I).

This reaction is carried out preferably in the presence of an acid or a base. Examples of the acid are sulfuric acid, hydrochloric acid and p-toluenesulfonic acid. Examples of the base are inorganic bases such as sodium hydroxide, potassium hydroxide, sodium carbonate and sodium hydrogen carbonate, and alkoxides such as sodium methoxide or potassium-t-butoxide.

In this reaction, an alcohol is formed. Since the reaction is an equilibrium reaction, it is preferable to remove the alcohol from the reaction system by, for example, distillation or azeotropic distillation. Accordingly, carboxylic acid ester of formula (B) in which $R^9$ is an alkyl group having 1 to 5 carbon atoms especially 1 to 3 carbon atoms, are preferably used as the starting material.

Generally, this reaction is carried out without a solvent. When the starting materials are solid, it is preferable to use a solvent having a higher boiling point than the by-product alcohol.

Examples of a solvent that can be suitably used are aromatic hydrocarbons or halogenated aromatic hydrocarbons such as benzene, toluene, xylene, chlorobenzene and dichlorobenzene, N,N-dialkylamides such as N,N-dimethylformamide and N, N-diethylformamide, and dimethyl sulfoxide.

The temperature for the reaction differs according to the type of the by-product alcohol. Generally, the temperature at which the by-product alcohol distills is preferred. The reaction time differs depending upon the type of the starting materials. Usually, it is chosen from 30 minutes to 24 hours, preferably 2 to 8 hours. Preferably the reaction is carried out with stirring.

There is no limitation on the method of isolating the desired compound of formula (I) from the reaction system and purifying it, and any known methods may be employed.

The sulfur-containing unsaturated compounds of formula (I) readily undergo polymerization in the presence of radical polymerization initiators to be described to give polymers which are colorless and transparent and have a high refractive index, a low specific gravity and excellent impact strength.

The sulfur-containing unsaturated compounds of formula (I), when polymerized alone, can give the desired polymers having a high refractive index. Frequently, they may be preferably copolymerized with other unsaturated compounds copolymerizable with the sulfur-containing unsaturated compounds of formula (I) to adjust the refractive indices or other properties of the resulting polymers or to make easy the polymerization of these compounds. The copolymerizable other unsaturated compounds may be selected according to the purposes without any particular restriction. Because the sulfur-containing unsaturated compounds of formula (I) are liquid and have good compatibility, even solid unsaturated compounds can advantageously be used as comonomers. Examples of the copolymerizable other unsaturated compounds which can be suitably used include unsaturated carboxylic acids, unsaturated carboxylic acid esters, allyl compounds, aromatic vinyl compounds and unsaturated thiocarboxylic acid esters. More specific examples are unsaturated carboxylic acids such as acrylic acid, methacrylic acid, maleic anhydride and fumaric acid; unsaturated carboxylic acid esters, for example, acrylic and methacrylic acid esters such as methyl acrylate, methyl methacrylate, benzyl methacrylate, phenylmethacrylate, 2-hydroxyethyl methacrylate, ethylene glycol diacrylate, diethylene glycol dimethacrylate, bisphenol A dimethacrylate, 2,2-bis(4-methacryloxyethoxyphenyl)propane, 2,2-bis(3,5-dibromo-4-methacryloxyethoxyphenyl)propane and trifluoromethyl methacrylate, and fumaric acid esters such as monomethyl fumarate, diethyl fumarate and diphenyl fumarate; allyl compounds such as diallyl phthalate, diallyl terephthalate, diallyl isophthalate, diallyl tartarate, diallyl epoxysuccinate, diallyl maleate, allyl cinnamate, allyl isocyanate, diallyl chlorendate, diallyl carbonate and allyl diglycol carbonate; aromatic vinyl compounds such as styrene, alpha-methylstyrene, vinylnaphthalene, isopropenylnaphthalene, bromostyrene and dibromostyrene; and unsaturated thiocarboxylic acid esters such as methyl thiomethacrylate, ethyl thiomethacrylate, benzyl thiomethacrylate, phenyl thiomethacrylate, methyl thioacrylate, benzyl thioacrylate and phenyl thioacrylate.

Frequently, the presence in the reaction system of an unsaturated epoxy compound, an unsaturated urethane compound or an oligomer of an unsaturated carboxylic acid ester is an effective means for stabilizing the polymerization system or improving the properties of the resulting polymer in the polymerization of the above monomer or monomeric mixture in this invention. There is no particular limitation on these additive components. Typical examples include unsaturated epoxy acrylates and unsaturated epoxy methacrylates such as 2-hydroxy-3-phenoxypropylacrylate, 2-hydroxy-3-phenoxypropyl methacrylate, polyethylene glycol diglycidyl ether/methacrylic acid adduct, propylene glycol diglycidyl ether/methacrylic acid adduct, glycerol diglycidyl ether/acrylic acid adduct and bisphenol A diglycidyl ether/methacrylic acid adduct; unsaturated urethane compounds such as a hexa-methylene diisocyanate adduct of phenyl glycidyl ether/methacrylic acid, a toluene diisocyanate adduct of phenyl glycidyl ether/methacrylic acid adduct, an isophorone diisocyanate adduct of glycerol dimethacrylate/-isophutrone diisocyanate adduct and pentaerythritol triacrylate/hexamethylene diisocyanate adduct; and oligomers of unsaturated carboxylic acid esters, for example unsaturated polyesters such as a polyester compound composed of maleic anhydride and diethylene glycol and a polyester compound composed of maleic anhydride, phthalic anhydride and hexamethylenediol.

The sulfur-containing unsaturated compounds of formula (I), the copolymerizable other unsaturated compounds, and the unsaturated epoxy compounds etc to be optionally used may be respectively used singly or in a combination of two or more.

As required, polymerization may be carried out by using a solvent. There is no particular limitation on the solvent, and known solvents may properly be selected as required Examples of especially suitable solvents for the polymerization are aliphatic hydrocarbons such as hexane and cyclohexane; aromatic hydrocarbons such as benzene, toluene and xylene; ethers such as tetrahydrofuran and propyl ether; ketones such as cyclohexanone and acetone, esters such as ethyl acetate; alcohols such as ethanol and isopropanol, and halogenated hydrocarbons such as chloroform.

The copolymerizable unsaturated compounds are selected according to the properties required of the polymer to be obtained. When the sulfur-containing unsaturated compound of formula (I) which has only one polymerizable group is to be homopolymereized, injection molding can give a polymer having the desired shape. When a copolymer of the compound of formula (I) is desired, a monomer having only one polymerizable group must be selected as another copolymerizable unsaturated compound. When the resulting polymer having a high refractive index has to be processed, for example, ground, it is advantageous to use an unsaturated compound having at least two polymerizable groups and copolymerize and crosslink the sulfur-containing unsaturated compound of formula (I) with this comonomer thereby giving a crosslinked copolymer.

The amount of the copolymerizable other unsaturated compound to be mixed varies depending upon the properties required of the copolymer to be obtained, but is generally 20 to 500 parts by weight, preferably 20 to 200 parts by weight, per 100 parts by weight of the sulfur-containing unsaturated compound. Known radical polymerization may be employed in polymerizing the sulfur-containing unsaturated compound of formula (I) alone or with the polymerizable other unsaturated compound. For initiation of the polymerization of the above monomer or the monomeric mixture, a radical polymeriation initiator such as peroxides, azo compounds or the irradiation of ultraviolet light, alpha-rays, beta-rays, gamma-rays, etc. may be used.

Examples of the radical polymerization initiators include diacyl peroxides such as benzoyl peroxide, p-chlorobenzoyl peroxide, decanoyl peroxide, lauroyl peroxide and acetyl peroxide, peroxy esters such as t-butyl peroxy-2-ethyl hexanate, t-butylperoxy neodecanate, and t-butyl peroxybenzoate; peroxydicarbonates such as diisopropyl peroxydicarbonate, di-2-ethylhexyl peroxydicarbonate and di-sec-butylperoxydicarbonate; and azo compounds su h as azobisisobutyronitrile. The amount of the radical polymerization initiator used varies depending upon the polymerization conditions, the type of the initiator and the monomer composition, but is generally 0.01 to 10 parts by weight, preferably 0.01 to 5 parts by weight, per 100 parts by weight of the monomer or the monomeric mixture to be polymerized.

The temperature, among the polymerization conditions, particularly affect the properties of the resin having a high refractive index to be obtained. This temperature condition is in turn affected by the type and amount of the initiator and the type of the monomer. Generally, it is suitable that the polymerization is initiated at a relative low temperature, and the temperature is slowly raised, and at the final stage of the polymerization curing is carried out at a high temperature (so-called tapered two-step polymerization). The polymerization time varies depending upon various factors as does the polymerization temperature It is proper to determine the optimal time in advance according to these factors. Generally, it is preferable to choose conditions under which the polymerization will be completed in 2 to 40 hours.

Known polymerization procedures may be employed. For example, cast polymerization may be preferably employed by which the above monomer or monomeric mixture containing a radical polymerization initiator is poured into a mold supported by an elastomer gasket or a spacer, polymerized and cured in an air furnace, and then taken out.

It is also possible to select the monomer of formula (I) or a mixture of monomers each having one polymerizable group, prepolymerize it to obtain a prepolymer and then polymerize and mold it. Or it may be polymerized to pellets and then molded into the desired shape by injection molding or extrusion molding.

To obtain the prepolymer or pellets, there can be used, for example, bulk polymerization, solution polymerization, emulsion polymerization, suspension polymerization, and sedimentation polymerization.

As can be understood from the above-described polymerization methods, the present invention provides a homo —or co-polymer consisting substantially of polymer units derived from at least one sulfur-containing unsaturated compound of formula (I), and a random copolymer consisting substantially of polymer units derived from at least one sulfur-containing unsaturated compound of formula (I) and polymer units derived from at least one other unsaturated compound copolymerizable with the sulfur-containing unsaturated compound of formula (I).

These polymers of the invention have a high refractive index. Preferably, they have a refractive index of at least 1.62, especially at least 1.63 and an Abbe number of at least 30, especially at least 32.

The resin of this invention having a high refractive index is the above polymer or copolymer. It may contain various additives and stabilizers added at the time of polymerization, such as a mold releasing agent, an ultraviolet absorber, an antioxidant, a coloration inhibitor, an antistatic agent, a fluorescent dye, a dye and a pigment.

Depending upon the end use, the resin of this invention having a high refractive index can be subjected to the following treatments. For example, specifically, it may be dyed with a disperse dye, etc. A hard coated layer composed as a main component of a sol of an oxide such as an oxide of silicon, zirconium, antimony or aluminum, or a silane coupling agent, or an organic polymer. It may be treated for prevention of reflection by vacuum-evaporating a thin film of a metal oxide such as $SiO_2$, $TiO_2$ or $ZrO_2$ or coating a thin film of an organic polymer. It may also be processed or subjected to a secondary treatment for antistatic prevention.

The resins of this invention having a high refractive index have excellent hardness, impact strength and lightweight, and are therefore useful as optical lenses such as eyeglass lenses and lenses for optical instruments. They can also be suitably used as prisms, optical disc substrates and optical fibers.

The following examples are given to illustrate the invention specifically. It should be understood that the present invention is not limited to these examples.

The compounds in the following examples were analyzed and identified by the following methods.

(1) IR spectrum

The instrument (IR-440 type made by Shimazu Seisakusho Co., Ltd.) was used. The sample in thin film form was held by KBr plates and subjected to IR spectrum measurement.

(2) $^1H$-NMR spectrum

Measured by using an instrument (PMX-60Sl type (60 MHz made by JEOL Co., Ltd.) The sample was diluted with $CDCl_3$, and its $^1H$-NMR spectrum was measured using tetramethylsilane as an internal standard (3) Elemental analysis Carbon and hydrogen were analyzed by using a CHN corder (MT-2 type made by Yanagimoto Seisakusho K.K.) Sulfur was measured by using the flask combustion method (4) Refractive index ($\eta_D^{20}$)

The refractive index of the sample at 20° C. was measured by an Abbe refractometer (3T type, made by Atago Co., Ltd).

The properties of the resins having a high refractive index obtained in the examples were measured by the following methods.

(1) Refractive index ($\eta_D^{20}$) and Abbe number

By using an Abbe refractometer (3T type), the refractive index and Abbe number of the sample at 20° C. were measured using bromonaphthalene or methylene iodide as a contact liquid (2) Appearance Evaluated by visual observation.

(3) Durability

The sample was set on a long-life xenon fade meter (FAC-25AX-HC type made by Suga Test Instruments Co., Ltd.), and exposed to xenon light for 100 hours The degree of coloration was then visually observed, and rated on the following scale.

◯: the degree of coloration was lower than that of polystyrene

Δ: the degree of coloration was equivalent to that of polystyrene

X: the degree of coloration was higher than that of polystyrene.

(4) Impact resistance

A steel ball having a predetermined weight was let fall spontaneously from a height of 127 cm onto a circular sample plate having a thickness of 2 mm and a diameter of 65 mm. The limit of weight of the ball which did not break the sample plate was measured.

The above measurement was carried out on 20 sample plates. The maximum and minimum weights measured were excluded, and the measured weights of the remaining 18 sample plates were averaged to obtain an average value (g), and the impact resistance of the sample was this average value.

(5) Adhesion of the hard coated film

A plate-like sample resin was fully washed with methanol and air-dried to make it clean and clear. The resin plate was then immersed for 10 minutes in a 10% aqueous solution of sodium hydroxide. Then, it was washed with water and dried to pre-treat the sample. Separately, a hard coating liquid was prepared by sufficiently mixing 20 parts by weight of bis(gamma-triethoxysilylpropyl)carbonate, 10 parts by weight of gammaglycidoxypropyltrimethoxysilane, 30 parts by weight of colloidal silica (methonol sol made by Nissan Chemical Co., Ltd.), 30 parts by weight of methyl cellosolve, 10 parts by weight of 0.05N hydrochloric acid, and 0.25 part by weight of ammonium perchlorate.

The pre-treated sample was dipped in the hard coating liquid, fully air dried at room temperature, and heated at 80° C. for 3 hours to cure the resulting coated film. The adhesion of the coated film obtained was evaluated by the following test. One hundred squares, 1 mm ×1 mm, were provided on the surface of the sample by a cutter knife with a sharp tip, and a commercial adhesive tape was applied onto these squares. It was then quickly peeled off, and the state of peeling of the coated film was visually observed The result was evaluated by the number of squares which remained unpeeled out of 100 squares.

(6) Tintability

Two grams of a disperse dye (Vista brown, a product of Hattori Seiko Co., Ltd.) was dispersed in 1 liter of water, and heated to 90° C. The resin sample which could be dyed with the resulting dye dispersion was rated as 0, and that which could not be dyed with it was rated as X.

(7) Grinding properties

The sample plate was ground by using an auto lens edger (ALE-60 type made by Tokyo Optical Machine Co., Ltd.). The sample which could be ground was rated as 0, and that which could not, as X.

(8) Hardness

The hardness on L-scale of a test plate having a thickness of 2 mm was measured by using a Rockwell durometer.

In the following Examples, the following abbreviations were used for monomers.

Br$_3$PhMA 2,4,6-tribromophenyl methacrylate
ClSt: chlorostyrene
BDMA: 2,2',6,6'-tetrabromo bisphenol A dimeth-acrylate
DEGM: diethylene glycol dimethacrylate
DAIP: diallyl isophthalate
BMEPP: 2,2-bis(4-methacryloyloxyethoxyphenyl)-propane propane
α-MeSt: αmethylstyrene
BBMEPP: 2,2-bis(3,5-dibromo-4-methacryloyloxyethoxyphenyl)propane
HEMA: 2-hydroxyethyl methacrylate
St: styrene
PETM: pentaerythritol tetramethacrylate
DVB: divinylbenzene
VDF: 2-vinyldibenzofuran
TMTM: methyl thiomethacrylate
TBTM: benzyl thiomethacrylate
AA: acrylic acid
MA: methacrylic acid
U-4A: urethane acrylate (NK Oligo U-4HA, a tradename for a product of Shin Nakamura Kagaku Kogyo K.K.)
EB-810: polyester acrylate (EB-810, a tradename for a product of Daicell UCB Co., Ltd.)
40EM: unsaturated epoxy compound (Epoxyester 40EM, a tradename for a product of Kyoueisha Yushi Kagaku Kogyo K. K.).

EXAMPLE 1

A three-necked flask equipped with a thermometer, a stirrer and a dropping funnel was charged with 20.2 g (0.11 mole) of 2-benzylthioethylthiol, 12.2 g (0.13 mole) of triethylamine and 100 ml of anhydrous chloroform, and the mixture was cooled to 0°. With stirring, 12.6 g (0.12 moles) of methacryloyl chloride was gradually added dropwise. At this time, the reaction temperature was maintained at 0° to 5° C., and after the addition, the mixture was further stirred at 20° C. for 1 hour. Then, the reaction mixture was poured into water, and the organic layer was washed with a dilute aqueous solution of sodium carbonate, followed by washing with water. The organic layer was dried over anhydrous magnesium sulfate, and the solvent was removed by distillation under reduced pressure. The resulting oil was distilled under reduced pressure to give 16.3 g of the desired 2-benzylthioethyl thiomethacrylate having a boiling point of 132° to 135° C. (0.05 mmHg) as a colorless clear liquid. This product had a refractive index of 1.584. The IR chart of this compound is shown in FIG. 1. A strong absorption based on the carbonyl group was observed at 1670 cm$^{-1}$, and an absorption based on the terminal double bond was observed at 1640 cm$^{-1}$. The $^1$H-NMR (in CDCl$_3$ solvent, internal standard tetramethylsilane, ppm) chart of this compound is shown in FIG. 2. Three peaks attributed to the hydrogen (c) of the methyl group at δ1.93 as a doublet with a coupling constant of 2 Hz, four peaks at δ2.4 -3.3 ascribed to hydrogens (d) and (e) of the methylene group as a multiplet, two peaks attributed to the hydrogen (f) at the benzyl position at δ3.76 as a singlet, one peak attributed as the hydrogen (a) of the vinyl group at δ5.56 as a multiplet, one peak attributed to the hydrogen (b) of the vinylidene group at δ6.06 as a multiplet, and five peaks attributed to the hydrogen (g) of the phenyl group at δ7.1 as a multiplet were each observed.

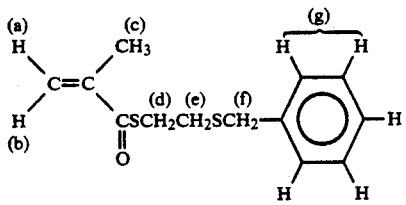

The elemental analysis values (the parenthesized values were calculaged values) well agreed with the calculated values.

C: 61.81 % (61.86 %), H: 6.09 % (6.39 %), S: 25.33 % (25.41 %).

EXAMPLE 2

A three-necked flask fitted with a thermometer, a stirrer and a dropping funnel was charged with 21.6 g (0.20 mole) of 2-methylthioethylthiol, 17.4 g (0.22 mole) of pyridine and 200 ml of anhydrous benzene, and the mixture was cooled to 0° C. With stirring, 21.9 g (0.21 mole) of methacryloyl chloride was gradually added dropwise. At this time, the reaction temperature was maintained at 0° to 5° C. After the addition, the mixture was further stirred at 20° C. for 1 hour. Thereafter, the reaction mixture was poured into water, and the organic layer was washed with a dilute aqueous solution of sodium carbonate, and washed with water. The organic layer was dried over anhydrous magnesium sulfate, and the solvent was removed by distillation under reduced pressure. The resulting oil was distilled under reduced pressure to give 26.4 g of the desired 2-methylthioethyl thiomethacrylate as a colorless clear liquid having a boiling point of 100° to 105° C. (8 mmHg). This compound has a refractive index of 1.540. Its elemental analyisis values (the parenthesized values were calculated values) well agreed with the calculated values. C: 47.38% (47.69%), H: 7.04% (6.86%), S: 31.39% (31.57%).

EXAMPLE 3

Three-necked flask fitted with a thermometer, a stirrer and a dropping funnel was charged with 16.8 g (0.10 mole) of di(2-mercaptoethyl)sulfide monomethyl thioether, 11.1 g (0.11 mole) of triethylamine, and 100 ml of anhydrous chloroform, and the mixture was cooled to 0° C. With stirring, 10.0 g (0.11 mole) of acryloyl chloride was gradually added dropwise At this time, the reaction temperature was maintained at 0° to 5° C. After the end of addition, the mixture was further stirred at 20° C. for 1 hour Then, the reaction mixture was poured into water. The organic layer was washed with a dilute aqueous solution of sodium carbonate, and then with water. The organic layer was dried over anhydrous magnesium sulfate. The resulting oil was purified by column chromatography (filler: silica gel; developing agent: chloroform) to give 23.1 g of acryloylthioethyl 2-methylthioethyl sulfide as a colorless clear oil. This compound had a refractive index of 1.585. In its IR spectrum, a strong absorption based on the carbonyl group at 1765 cm$^{-1}$ and an absorption based on the terminal double bond at 1640 cm$^{-1}$ were observed. Its elemental analysis values (the parenthesized values were calculated values) well agreed with the calculated values.. C: 43.26 % (43.21%), H: 6.58% (6.36%), S: 42.98% (43.26%).

EXAMPLE 4

The thiocarboxylic acid esters indicated in Table 1 were prepared in the same way as in Example 3 using various starting materials. The properties of the resulting thiocarboxylic acid ester compounds are given in Table 1.

TABLE 1

| Run No. | Sulfur-containing unsaturated compound No. | Property | Refractive index D | IR (cm$^{-1}$) (C = 0) | Values of elemental analysis (%) calculated values in parentheses | | |
|---|---|---|---|---|---|---|---|
| | | | | | C | H | S |
| 1 | 100 | colorless transparent liquid | 1.545 | 1665 | 47.57 (46.69) | 6.99 (6.86) | 36.52 (36.38) |
| 2 | 102 | colorless transparent liquid | 1.579 | 1670 | 45.70 (45.72) | 6.58 (6.82) | 40.77 (40.69) |
| 3 | 104 | colorless transparent viscous liquid | 1.587 | 1670 | 44.38 (44.55) | 7.03 (6.80) | 42.96 (43.25) |
| 4 | 106 | colorless transparent liquid | 1.584 | 1665 | 59.04 (58.89) | 6.38 (5.39) | 28.43 (28.59) |
| 5 | 108 | colorless transparent liquid | 1.580 | 1670 | 61.56 (61.86) | 6.40 (6.39) | 25.49 (25.41) |
| 6 | 110 | colorless transparent viscous liquid | 1.604 | 1670 | 36.52 (36.38) | 3.21 (3.05) | 16.35 (16.19) |
| 7 | 112 | colorless transparent liquid | 1.600 | 1670 | 55.02 (54.89) | 5.91 (5.67) | 34.10 (33.82) |
| 8 | 114 | colorless transparent liquid | 1.598 | 1670 | 68.47 (68.75) | 5.53 (5.77) | 20.56 (20.39) |

EXAMPLE 5

In each run, 100 parts by weight of each of the sulfur-containing unsaturated compounds indicated in Table 2 produced in accordance with examples 1 to 4 was well mixed with 1 part by weight of t-butyl peroxy2-ethylhexanate as a radical polymerization initiator. The mixture was poured into a mold constructed of two glass plates and a gasket composed of an ethylene/vinyl acetate copolymer, and cast-polymerized. The polymerization was carried out in an air furnace, and the temperature was gradually added from 30° C. to 90° C. over 18 hours, and the reaction mixture was maintained at 90° C. for 2 hours. After the end of polymerization, the mold was taken out from the air furnace, and allowed to cool. The resulting polymer was removed from the glass plates of the mold. The properties of the polymer were measured, and the results are shown in Table 2.

TABLE 2

| Run No. | Sulfur-containing unsaturated compound No. | Appearance | Specific gravity | Refractive index | Abbe number | Impact resistance | Adhesion of the coated film | Durability |
|---|---|---|---|---|---|---|---|---|
| 1 | 116 | colorless transparent | 1.23 | 1.609 | 36 | 130 | 100 | o |
| 2 | 100 | " | 1.23 | 1.607 | 36 | 128 | " | o |
| 3 | 118 | " | 1.35 | 1.618 | 36 | 95 | " | o |
| 4 | 120 | " | 1.21 | 1.603 | 37 | 110 | " | o |
| 5 | 122 | " | 1.22 | 1.605 | 36 | 105 | " | o |
| 6 | 124 | " | 1.24 | 1.659 | 32 | 108 | " | o |
| 7 | 126 | " | 1.26 | 1.639 | 34 | 142 | " | o |
| 8 | 102 | " | 1.24 | 1.617 | 35 | 141 | " | o |
| 9 | 104 | " | 1.26 | 1.639 | 34 | 150 | " | o |
| 10 | 132 | " | 1.23 | 1.637 | 34 | 116 | " | o |
| 11 | 134 | " | 1.32 | 1.641 | 34 | 103 | " | o |
| 12 | 136 | " | 1.83 | 1.675 | 32 | 84 | " | o |
| 13 | 138 | " | 1.71 | 1.655 | 34 | 100 | " | o |
| 14 | 140 | " | 1.81 | 1.658 | 34 | 95 | " | o |
| 15 | 142 | " | 1.23 | 1.625 | 35 | 110 | " | o |
| 16 | 144 | " | 1.20 | 1.621 | 35 | 105 | " | o |
| 17 | 146 | " | 1.24 | 1.643 | 34 | 101 | " | o |
| 18 | 148 | " | 1.27 | 1.656 | 33 | 98 | " | o |
| 19 | 150 | " | 1.20 | 1.646 | 33 | 95 | " | o |
| 20 | 152 | " | 1.24 | 1.659 | 33 | 94 | " | o |
| 21 | 108 | " | 1.23 | 1.635 | 34 | 113 | " | o |
| 22 | 156 | " | 1.22 | 1.630 | 35 | 107 | " | o |
| 23 | 158 | " | 1.24 | 1.650 | 33 | 142 | " | o |
| 24 | 160 | " | 1.43 | 1.657 | 33 | 131 | " | o |
| 25 | 162 | " | 1.25 | 1.660 | 32 | 153 | " | o |
| 26 | 164 | " | 1.21 | 1.632 | 34 | 111 | " | o |
| 27 | 166 | " | 1.20 | 1.627 | 35 | 108 | " | o |
| 28 | 106 | " | 1.26 | 1.649 | 32 | 105 | " | o |
| 29 | 170 | " | 1.24 | 1.619 | 33 | 103 | " | o |
| 30 | 112 | " | 1.27 | 1.653 | 29 | 98 | " | o |
| 31 | 114 | " | 1.20 | 1.656 | 32 | 93 | " | o |
| 32 | 172 | " | 1.24 | 1.661 | 29 | 90 | " | o |
| 33 | 174 | " | 1.26 | 1.656 | 30 | 143 | " | o |
| 34 | 176 | " | 1.25 | 1.641 | 31 | 138 | " | o |
| 35 | 153 | " | 1.21 | 1.631 | 34 | 110 | " | o |
| 36 | 154 | " | 1.20 | 1.626 | 35 | 105 | " | o |

COMPARATIVE EXAMPLE 1

Example 5 was repeated except that the sulfur-containing unsaturated compounds indicated in Table 3 were used. The properties of the resulting polymers were as shown in Table 3.

compounds of the following formula shown in Table 4

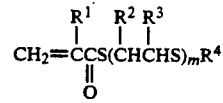

TABLE 3

| No. | Monomeric compound | Appearance | Specific gravity | Refractive index | Abbe number | Impact resistance | Adhesion of the coated film | Durability |
|---|---|---|---|---|---|---|---|---|
| 1 | $CH_2=CCH_3COSCH_3$ | colorless transparent | 1.20 | 1.587 | 35 | 33 | 100 | o |
| 2 | $CH_2=CCH_3COOCH_2CH_2SCH_3$ | colorless transparent | 1.19 | 1.521 | 43 | 65 | 20 | o |
| 3 | $\underset{CH_2=CCOSCH_2CH_2SOCC=CH_2}{\overset{CH_3 \qquad\qquad CH_3}{| \qquad\qquad\qquad |}}$ | colorless transparent | 1.25 | 1.612 | 33 | 25 | 100 | o |

EXAMPLE 6

Example 5 was repeated except that instead of the sulfur-containing unsaturated compounds, a monomeric mixture of each of the sulfur-containing unsaturated and a comonomer copolymerizable with the sulfur-containing unsaturated compound was used. The properties of the resulting polymers are shown in Table 4.

TABLE 4

| Run No. | Sulfur-containing unsaturated compound kinds number | added amount parts by weight | Comonomer kinds | added amount parts by weight | Appearance | Specific gravity | Refractive index | Abbe number | Durability | Hardness (HL) | Adhesion of the coated film | Impact resistance | Tintability | Grinding properties |
|---|---|---|---|---|---|---|---|---|---|---|---|---|---|---|
| 1 | 132 | 80 | BDMA | 20 | colorless transparent | 1.30 | 1.630 | 34 | ○ | 98 | 100 | 93 | ○ | ○ |
| 2 | " | 60 | " | 40 | colorless transparent | 1.37 | 1.624 | 34 | ○ | 105 | " | 71 | ○ | ○ |
| 3 | " | 80 | Br3PhMA | 20 | colorelss transparent | 1.35 | 1.635 | | ○ | | " | | | |
| 4 | " | 60 | " | 40 | colorless transparent | 1.47 | 1.633 | | ○ | | " | | | |
| 5 | | 80 | DEGM | 20 | colorless transparent | 1.23 | 1.611 | 37 | ○ | 88 | " | 101 | ○ | ○ |
| 6 | " | 60 | BMEPP α-MeSt | 30 10 | colorless transparent | 1.22 | 1.606 | 35 | ○ | 101 | " | 85 | ○ | ○ |
| 7 | " | 80 | BMEPP | 20 | colorless transparent | 1.37 | 1.624 | 34 | ○ | 103 | " | 92 | ○ | ○ |
| 8 | " | 50 | BBMEPP | 50 | colorless transparent | 1.22 | 1.621 | 34 | ○ | 119 | " | 81 | ○ | ○ |
| 9 | " | 60 | BMEPP U-4A | 30 10 | colorless transparent | 1.22 | 1.605 | 34 | ○ | 102 | " | 90 | ○ | ○ |
| 10 | " | 60 | BMEPP EB-810 | 30 10 | colorless transparent | 1.22 | 1.605 | 34 | ○ | 103 | " | 93 | ○ | ○ |
| 11 | " | 60 | BMEPP 40EM | 30 10 | colorless transparent | 1.22 | 1.605 | 34 | ○ | 104 | " | 84 | ○ | ○ |
| 12 | " | 80 | HEMA | 20 | colorless transparent | 1.24 | 1.614 | | ○ | | " | | | |
| 13 | 134 | 60 | BBMEPP | 40 | colorless transparent | 1.42 | 1.625 | 34 | ○ | 107 | " | 65 | ○ | ○ |
| 14 | 138 | 50 | BMEPP | 50 | colorless transparent | 1.46 | 1.628 | 34 | ○ | 113 | " | 60 | ○ | ○ |
| 15 | 158 | 80 | PETM | 20 | colorless transparent | 1.23 | 1.622 | 34 | ○ | 90 | " | 96 | ○ | ○ |
| 16 | 108 | 50 | BMEPP | 50 | colorless transparent | 1.22 | 1.618 | 34 | ○ | 100 | " | 84 | ○ | ○ |
| 17 | 106 | 50 | Br3PhMA | 50 | colorless transparent | 1.43 | 1.637 | | ○ | | " | | | |
| 18 | " | 60 | BBMEPP | 40 | colorless transparent | 1.39 | 1.629 | 32 | ○ | 110 | " | 85 | ○ | ○ |
| 19 | 116 | 50 | BDMA | 50 | colorless transparent | 1.41 | 1.607 | 35 | ○ | 110 | " | 85 | ○ | ○ |
| 20 | 102 | 60 | PETM | 40 | colorless transparent | 1.21 | 1.598 | 39 | ○ | 91 | " | 93 | ○ | ○ |
| 21 | 132 | 60 | ClSt | 40 | colorless transparent | 1.16 | 1.626 | | ○ | | 100 | | | |
| 22 | " | 60 | Br2St | 40 | colorless transparent | 1.50 | 1.645 | | ○ | | " | | | |
| 23 | " | 60 | BDF | 40 | colorless transparent | 1.22 | 1.654 | | ○ | | " | | | |
| 24 | " | 40 | " | 60 | colorless transparent | 1.21 | 1.662 | | ○ | | " | | | |
| 25 | " | 80 | DVB | 20 | colorless transparent | 1.20 | 1.633 | 33 | ○ | 112 | " | 84 | ○ | ○ |
| 26 | 142 | 60 | St | 40 | colorless transparent | 1.16 | 1.611 | | ○ | | " | | | |
| 27 | 178 | 60 | St | 40 | colorless transparent | 1.16 | 1.613 | | ○ | | " | | | |
| 28 | 180 | 60 | St | 40 | colorless transparent | 1.16 | 1.600 | | ○ | | " | | | |
| 29 | 182 | 60 | St | 40 | colorless transparent | 1.17 | 1.620 | | ○ | | " | | | |
| 30 | 150 | 60 | St | 40 | colorless transparent | 1.15 | 1.624 | | ○ | | " | | | |
| 31 | 152 | 60 | St | 40 | colorless transparent | 1.17 | 1.631 | | ○ | | " | | | |
| 32 | 158 | 80 | DVB | 20 | colorless transparent | 1.20 | 1.655 | 32 | ○ | 88 | " | 93 | ○ | ○ |
| 33 | 106 | 50 | clSt | 50 | colorless transparent | 1.24 | 1.630 | | ○ | | " | | | |
| 34 | 170 | 50 | " | 50 | colorless transparent | 1.20 | 1.615 | | ○ | | " | | | |
| 35 | 112 | 50 | " | 50 | colorless transparent | 1.24 | 1.631 | | ○ | | " | | | |
| 36 | 114 | 50 | " | 50 | colorless transparent | 1.22 | 1.629 | | ○ | | " | | | |

TABLE 4 -continued

| Run No. | Sulfur-containing unsaturated compound kinds number | added amount parts by weight | Comonomer kinds | added amount parts by weight | Appearance | Specific gravity | Refractive index | Abbe number | Durability | Hardness (HL) | Adhesion of the coated film | Impact resistance | Tintability | Grinding properties |
|---|---|---|---|---|---|---|---|---|---|---|---|---|---|---|
| 37 | 172 | 50 | " | 50 | colorless transparent | 1.42 | 1.636 | | o | | " | | | |
| 38 | 116 | 50 | " | 50 | colorless transparent | 1.14 | 1.610 | | o | | " | | | |
| 39 | " | 50 | BDF | 50 | colorless transparent | 1.22 | 1.644 | | o | | " | | | |
| 40 | 102 | 60 | DVB | 40 | colorless transparent | 1.21 | 1.640 | 32 | o | 94 | " | 88 | o | o |
| 41 | 132 | 60 | TMAM | 40 | colorless transparent | 1.22 | 1.617 | | o | | " | | | |
| 42 | " | 50 | TMAB | 50 | colorless transparent | 1.22 | 1.640 | | o | | " | | | |
| 43 | 106 | 50 | TMAM | 50 | colorless transparent | 1.23 | 1.618 | | o | | " | | | |
| 44 | 132 | 80 | MA | 20 | colorless transparent | 1.22 | 1.610 | | o | | " | | | |
| 45 | 106 | 90 | AA | 10 | colorless transparent | 1.25 | 1.634 | | o | | " | | | |
| 46 | 132 | 80 | DAIP | 20 | colorless transparent | 1.23 | 1.623 | 34 | o | 80 | " | 105 | o | o |
| 47 | 156 | 50 | St | 50 | colorless transparent | 1.14 | 1.610 | | o | | " | | | |

COMPARATIVE EXAMPLE 2

Example 6 was repeated except that instead of the monomeric mixture used in Example 6, a monomeric mixture composed of 50 parts by weight of

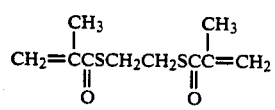

and 50 parts by weight of styrene was used. The resulting polymer had a colorless and transparent appearance, a specific gravity of 1.15, a refractive index of 1.601, an Abbe number of 31, a hardness of 115, a coated film adhesion of 100, an impact resistance of 40 g, good durability and good grinding properties. Its tintability was poor.

We claim:

1. A resin having a high refractive index and a high ABBE number, said resin being a polymer comprising units derived from a sulphur-containing unsaturated compound represented by the formula (II):

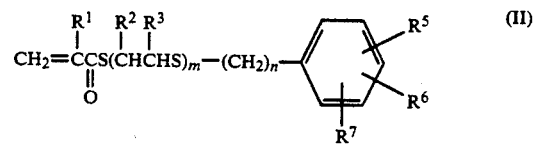

wherein $R^1$ represents a hydrogen atom or a methyl group; $R^2$ and $R^3$ are identical or different and each represents a hydrogen atom, methyl group or ethyl group; and

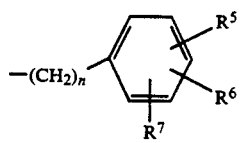

represents benzyl, pehnylethyl, phenylpropyl, phenylbutyl, chlorophenylmethyl, dibromophenylmethyl, tribromophenylmethyl, methylthiophenylmethyl, di(methylthio)phenylmethyl, or methylphenylmethyl, and m is 1, 2 or 3.

2. The resin of claim 1 in which the polymer has a refractive index of at least 1.62 and an ABBE number of at least 30.

3. The resin of claim 1 in which the polymer has a refractive index of at least 1.63 and an ABBE number of at least 32.

* * * * *